United States Patent [19]

Chen

[11] 4,303,589

[45] Dec. 1, 1981

[54] HYDROESTERIFICATION PROCESS

[75] Inventor: Gordon T. Chen, St. Louis, Mo.

[73] Assignee: Monsanto Company, St. Louis, Mo.

[21] Appl. No.: 108,762

[22] Filed: Dec. 31, 1979

[51] Int. Cl.$^3$ .................. C11C 3/02; C07C 51/10; C07C 51/12

[52] U.S. Cl. .................. 260/410.9 R; 260/410.6; 260/413; 560/233; 568/451

[58] Field of Search .................. 260/410.6, 410.9 C, 260/410; 560/233

[56] References Cited

U.S. PATENT DOCUMENTS

| | | | |
|---|---|---|---|
| 3,507,891 | 4/1970 | Hearne et al. | 260/410.9 R |
| 3,856,832 | 12/1974 | Ethyl Corp. | 260/410.9 R |
| 3,980,683 | 9/1976 | Isa et al. | 260/410.9 C |
| 4,041,057 | 8/1977 | Fanning | 260/410.9 R |
| 4,102,922 | 7/1978 | Price | 260/410.9 C |

FOREIGN PATENT DOCUMENTS

| | | | |
|---|---|---|---|
| 850675 | 9/1970 | Canada | 260/410 |
| 51-114392 | 4/1975 | Japan | 260/410 |

*Primary Examiner*—John F. Niebling
*Attorney, Agent, or Firm*—Joseph D. Kennedy; James W. Williams, Jr.

[57] ABSTRACT

Hydroesterification of internal olefins over cobalt catalyst is conducted with high cobalt concentration, 170°–200° C., and 1200–1800 psi gauge to provide good reaction rate, effective product recovery and high normality of product, combined with good catalyst recovery and simple recycle procedure.

11 Claims, No Drawings

HYDROESTERIFICATION PROCESS

The present invention relates to an olefin hydroesterification process in which high concentrations of cobalt catalyst are employed under conditions to permit good reaction rate and selectivity to desired product with effective product recovery and catalyst recycle.

BACKGROUND OF THE INVENTION

The hydroesterification of olefins by reaction with carbon monoxide and alcohols, utilizing cobalt catalyst in the presence of pyridine, is a known process. However, various problems have been encountered in attempting to conduct the process under conditions for good catalyst stability and efficiency, good reaction rates and product selectivity, along with effective product recovery and catalyst recycle procedures. Low catalyst concentrations have generally been used because of concern over catalyst stability. Also relatively high pressures have often been employed to effect the reaction and enhance catalyst stability. Some described procedures have unacceptable reaction rates, particularly for internal olefin reactants which are less reactive. The procedures often emphasize α-olefin reactants, perhaps because of the tendency of internal olefins to produce branched products rather than linear products which are generally more desirable. There was some belief that normality of the ester increased with declining temperature and rising carbon monoxide pressure.

Problems have also been encountered in catalyst recovery or recycling. It is desirable to recycle the cobalt as a matter of efficiency and economics. In addition, cobalt when present causes difficulties in distillation of product, causing formation of high boiler material, and also often plating out in distillation apparatus. Conditions to improve catalyst recovery often have poor compatibility with conditions for effective reaction, or which are considered appropriate for catalyst stability during reaction.

While prior procedures set forth various conditions, they do not describe conditions including combinations of temperature, pressure and cobalt concentration suitable for achieving good reaction rate and high normal content of ester product, along with catalyst stability and recoverability.

SUMMARY OF THE INVENTION

It has now been found that the use of high cobalt concentration within a defined range, in combination with other prescribed conditions, permits a combination of good reaction rate and product selectivity together with an efficient product recovery and cobalt recycle. The process uses about 2% to 6% cobalt concentrations at temperatures of 170° to 200° C. and pressures of 1200 to 2,000 psi gauge, concentrations and conditions which might be expected to cause catalyst instability, and yet achieves good results with good catalyst stability. The cobalt catalyst in active form is separated from the ester product by a simple phasing procedure involving addition of a non-polar phasing agent, and because of the effect of the high cobalt concentration, the separation leaves only small amounts of cobalt in the ester product phase, e.g., less than 1% of the original cobalt, so that materials can be directly distilled from the product without undue formation of high boilers or interference from the cobalt.

DETAILED DISCLOSURE OF THE INVENTION

Olefin, carbon monoxide and lower alkanol are reacted at elevated temperature and pressure in in the presence of a high concentration of cobalt catalyst in solution. Cobalt is employed in about 2 to about 6 weight percent of the reaction solution (calculated as cobalt). Lesser amounts are not conducive to good reaction rates, particularly with internal olefin reactant. The reaction temperature should be high enough to give a good reaction rate, particularly with the internal olefin content, and in the range of about 170° or 180° to about 200° C. Higher temperatures lead to more by-product formation, and catalyst instability. The carbon monoxide pressure can vary considerably, but there is advantage in operating at moderate carbon monoxide pressures in the range of about 1200 to about 1800 psi. In the past there has been some belief that somewhat higher pressures were advisable to aid catalyst stability, but it has been found that the indicated range is satisfactory in this regard, and has advantage over higher pressures in lowering by-product formation; and also in contributing to product normality. With internal olefin reactants in particular, it has been found that normal ester product declines as pressure is increased. However, a certain threshold pressure is desirable in order to give a desirable reaction rate, and pressures of at least about 1200 psi are usually desirable. The cobalt concentration is especially important. With concentrations less than about 2-2½%, the reaction rate tends to be slow. In addition, at least 2½% cobalt is useful in helping catalyst separation; and also contributes to product recovery, as will be explained further hereinbelow. Desirable amounts of cobalt are in the range of about 2-2.5% to about 6% or so cobalt, the percentages being by weight of the reaction mixture. The cobalt catalyst is utilized in conjunction with a promoter, particularly a pyridine compound, including various substituted pyridines or pyridine derivatives. Pyridine itself can conveniently be used, but the other pyridines are also suitable. The pyridine will be used in an amount to give a suitable reaction rate, but there is ordinarily no advantage in increasing the pyridine beyond the amounts which significantly improve reaction rate, as this unnecessarily adds to volume of material handled. The desirable amounts of pyridine are in the range of about 2 to about 10 parts pyridine per part cobalt, on a molar basis.

Hydrogen has also been found to have a significant influence on reaction rate, and it is desirable to have hydrogen present in molar ratio to carbon monoxide in the range of about 0.02 to about 0.1; below this range, the reaction rate is lower, while there is excessive by-product formation above the range. The alcohol level also influences the reaction rate. On a stoichiometric basis, only one alcohol molecule is required to esterify each carboxyl group and therefore one for each olefin molecule converted to ester; however, there is advantage in employing excess alcohol, and with methanol as an exemplification, about 2 to 5 moles methanol per mole olefin reactant. Lower ratios give slower reaction rates, while higher ratios unnecessarily add to the volume of the reaction mixture. Excess methanol also aids in causing phasing of the reaction mixture.

In order to obtain good reaction rate and high product normality, the present invention employs relatively high temperature, low pressure and high cobalt level, which together point toward catalyst instability. The described ranges of conditions have been found an appropriate adjustment to provide good rate and product normality with acceptable catalyst stability. For example, at 180° C., 1500 psi gauge (5% $H_2$, balance CO), and 4% cobalt concentration, the internal dodecenes initially charged (methanol and pyridine medium) was 93% converted in 30 minutes, with 72% of the methyl ester produced being normal ester. The cobalt catalyst remained in solution for subsequent phasing and recycle as described hereinbelow.

The hydroesterification can be conducted under conditions resulting in a two-phase reaction product mixture upon cooling at atmospheric pressure, for example by utilizing only a small excess of methanol, particularly if the olefin is not taken to high conversion. However, if a large excess of methanol is utilized, as advisable for good rates, a single phase is produced, and it is desirable to force a phase separation by appropriate means, such as addition of a phasing agent. Non-polar materials, such as hydrocarbons, e.g., alkanes, petroleum ether or additional olefin are very effective. The phasing agent, e.g., n-heptane, is added in amount to achieve phasing, and in particular with the desired degree of separation of the cobalt from the organic phase and into the polar phase. With a 1:1 weight ratio of heptane to product medium, more than 98-99% of the cobalt can be caused to separate into the lower polar phase. While there will be some variation with particular product medium and phasing agent, in the amount of phasing agent needed to obtain a separation of better than 98% or 99% of the cobalt, 0.5 weight part of agent or more per weight part product medium can be used, and usually at least 1 weight part, and the process will ordinarily involve use of phasing agent, e.g., heptane or petroleum ether, in the range of 0.5 to 2 weight parts per weight part product medium. One class of materials suitable as phasing agents are fairly good solvents for the ester products of the hydroesterifications, and fairly poor solvents for the alkanol reactant, and such materials are usually non polar in character, such as hydrocarbons, such as alkanes and olefins, particularly in the $C_5$–$C_{20}$ range, e.g., methyl pentane, cyclohexane, heptane, eicosane, decane, and other straight chain and cyclic alkanes, or olefins as disclosed as reactants herein. Alkanes having 5 to 10 carbon atoms are preferred, or petroleum ethers or other mixtures of hydrocarbons. The cobalt component is polar in character.

With the high cobalt concentrations and appropriate phasing agent, good separation of the cobalt catalyst is obtained, generally better than 90 or 95% and often better than 98-99%. In such separations it is desirable that the amount of cobalt left in the organic medium be a very low portion of that medium, such as less than 0.1% or preferably less than 500 ppm. With such low amounts, the medium can be directly subjected to distillation steps, or to distillation along with hydrolysis steps, to recover ester or acid by distillation, without undue production of high boiler materials. The phasing-separation conditions can be adjusted together with the hydroesterification concentrations and conditions to obtain proper combinations to achieve the specified low cobalt levels in the organic medium.

A pyridine promoter is utilized in the present invention. Such promoters include pyridine itself and substituted pyridines such as halopyridines, alkylpyridines, acylpyridines, nitropyridines, quinolines, cyanopyridines, etc. As alkyl substituents, it is generally convenient to utilize lower alkyls, containing 1 to 6 carbon atoms, but such groups can contain up to 20 or more carbon atoms. If desired, pyridines not substituted in the ortho position can be used as disclosed in U.S. Pat. No. 3,507,891, such as 3-methylpyridine, 4-methylpyridine, etc. Pyridine and substituted pyridines as described in U.S. Pat. No. 3,856,832 can be used.

The hydroesterification process requires an alcohol along with the olefin reactant. Alcohols in general are capable of esterification reactions and can be utilized in the present hydroesterification. However the ester is often an intermediate to the acid, and the esterifying alcohol may be chosen for convenience, particularly using lower alkanols, such as those having 1 to 6 carbon atoms. Methyl alcohol is ordinarily preferred. However, higher alcohols can be used. In order to effect separations as described herein, it is necessary to have sufficient polar material present to cause phasing of the reaction product mixture upon addition of hydrocarbon, and this should be taken into account in selecting the alcohol and its amount.

The present invention is particularly useful for the hydroesterification of internal olefins, as such olefins are generally less reactive than terminal olefins, and the reaction conditions prescribed herein are particularly conducive to giving good reaction rates along with high normality of product, with internal olefins. Nevertheless, the use of high cobalt concentrations and the separation procedures described herein will be very useful for terminal olefins, and such use involving the good reaction rate and unexpected stability of such catalyst concentrations, along with good product separation from catalyst and catalyst recyclability, is another aspect of the present invention.

Olefinically unsaturated aliphatic hydrocarbons in general can be used in the present process. The olefins have at least one non-aromatic carbon-to-carbon double bond, and generally have no acetylenic unsaturation. A convenient group of olefins for use is aliphatic monoolefins of 8 to 18 carbon atoms, although higher or lower olefins can be used. Both branched and straight chain olefins can be used. Olefins having the number of carbon atoms appropriate for producing soap or detergent range acids are of especial interest. Individual olefins can be used, or mixtures containing a range of olefins of different molecular weights. Olefins of especial interest include a mixture comprising mainly $C_{11}$ to $C_{13}$ olefins, and producing by hydroesterification esters of $C_{12}$ to $C_{14}$ acids. If desired, the individual $C_{11}$, $C_{12}$ and $C_{13}$ olefins can be hydroesterified in accord with the present invention. Similarly, a mixture of $C_{10}$ to $C_{12}$ olefins can be utilized to obtain $C_{11}$ to $C_{13}$ acids. A range of $C_{10}$ to $C_{14}$ olefins in admixture is also of interest. As discussed herein, the present invention is particularly adapted for use with internal olefins to produce products of high normality, the olefin being isomerized in the process. However such internal olefins may be part of an olefinic mixture which also includes terminal olefins. The presence of the internal olefins in the reactant mixture will make the use of the reaction conditions herein advantageous, even though some of the conditions may not have particular significance with respect to the terminal olefin content. Various mixtures of olefins obtained by coupling, polymerization or dehydrogenation reactions can be used. Isomerized olefins, such as produced by disproportionating propene and butene can be used. There is advantage in being able to utilize internal olefins, as such are prominent in olefinic mixtures from some sources or from particular processes, and mixture of internal olefins may often be the least expensive olefin available. Suitable olefin mixtures are further known to the art, as described for example in U.S. Pat. Nos. 3,856,832 and 3,507,891. The internal olefin mixtures for use herein will generally have less than 20%, or possibly less than 10%, alpha or terminal olefin content.

The cobalt catalyst can be any active form of cobalt hydroesterification catalyst and is generally regarded as some complex of cobalt carbonyl with pyridine. Any cobalt compound capable of forming cobalt carbonyl under the hydroesterification conditions can be used. The active catalyst can be provided by introducing a preformed cobalt carbonyl such as cobalt octacarbonyl into the reaction zone, or by adding cobalt compounds, especially salts, e.g., cobalt nitrate, cobalt octanoate or salts of other $C_2$–$C_{30}$ alkanoic acids, cobalt acetate, cobalt chloride, cobalt sulfate, etc., which can form cobalt carbonyls. The amounts of cobalt catalyst discussed herein are the amounts of the cobalt metal itself, and all ranges, ratios and percentages of cobalt are based on the metal.

One of the principal objects of the present invention is to convert internal olefins to esters of acids of high normality at a good rate, i.e., to produce esters or acids in which the acids have a high percentage of terminal acids, e.g., better than 70%. The rate of the reaction will vary with catalyst concentration, temperature and pressure, but it is desirable to have a rate of at least $k=2$ $hr^{-1}$, and preferably of at least $k=4$ $hr^{-1}$. Within the parameters and particular ranges described herein, it is possible to select combinations to produce the stated minimum rates, with the stated minimum normality, and also to have a stable catalyst and appropriate procedure for catalyst separation and recycle.

EXAMPLE 1

The hydroesterifications specifically described herein were generally carried out in a 300-ml stainless steel autoclave. Cobalt catalyst, in the form of $Co_2(CO)_8$ and other components were placed into the autoclave under an argon blanket and heated to the designated reaction temperature, usually under an initial pressure of 1100 psi gauge carbon monoxide, and building up to desired pressure. Reaction was then initiated by charging the proper small amount of hydrogen. The addition of hydrogen was taken as zero time, although some olefin was already converted. Utilizing this procedure, an isomerized dodecene was reacted with carbon monoxide and methanol at 180° C., 1500 psi gauge, (5% $H_2$, balance CO), utilizing 4% by weight cobalt (metal basis) in a reaction mixture containing methanol in 2.5:1 molar ratio to dodecene, and pyridine in 5:1 molar ratio to cobalt. Olefin conversion of about 94% was obtained in 30 minutes, and the product typically contains 43–45% ester (methyl tridecanoate); about 3% acid (tridecanoic acid) and about 2% aldehyde. The molar selectivity from olefin to ester and acid is about 89%. Weight percent of major components in a single phase product mixture produced in accord with the foregoing was found to be: 10% methanol; 27% pyridine; 2.3% dodecenes; 2.1% aldehyde; 45.1% methyl tridecanoate; 1.6% acetal; and 3.88% cobalt. The single phase mixture, 130.4 grams, was mixed with an approximately equal weight of n-heptane (133.8 grams) in a separatory funnel, causing immediate phase segregation. The larger upper phase (215.8 grams) was light amber and the smaller lower phase (46.1 grams) was dark brown in color. Only 1% of the cobalt was in the upper phase while 99% was in the lower phase, and 97% of the ester was in the upper phase, as well as 98% of the heptane. Methanol was split 46% upper and 54% lower, and similarly pyridine was 47% in the upper phase and 53% in the lower. Thus by a simple procedure 99% of the cobalt catalyst has been separated from product and remains in a form for recycle. The product separation is also very good with 97% of the ester being in the upper phase from which it can be recovered by conventional means, e.g., distillation. It is also important that the amount of cobalt in the upper organic phase is very small, 0.0506 grams, or about 230 ppm, in order to minimize problems of by-product formation during the subsequent product distillation. Product can suitably be recovered by distillation as described hereinbelow. Hydroesterification under the described conditions gives molar selectivity of olefin to ester and acid of 89%, and at a very good rate, $k=6$ $hr^{-1}$. The dodecene utilized in the above procedure was isomerized $C_{12}$-olefin obtained by isomerizing an $\alpha$-$C_{12}$ olefin by heating with ion exchange resin for 3 hours under nitrogen. The percentage of 1-isomer in the resulting olefin was 3.5–4.5%.

EXAMPLE 2

Hydroesterifications were conducted in a 300 ml. autoclave under carbon monoxide (with hydrogen) at varying temperatures and pressures, employing a reaction mixture containing 2% by weight cobalt, 27% by weight pyridine, 45% by weight isomerized $C_{12}$ olefin and 22% by weight methanol (pyridine/cobalt mol ratio of 10, methanol/olefin of 2.5), with results as follows:

TABLE 1

| Pressure (psi) | Temperature (°C.) | K ($hr^{-1}$) | Normal Content of Ester (%) |
|---|---|---|---|
| 3,000 | 160 | 0.6 | 56 |
| 3,000 | 170 | 2.8 | 61 |
| 3,000 | 180 | 4.3 | 68 |
| 3,000 | 190 | 5.0 | 71 |
| 3,000 | 200 | 5.2 | 71 |
| 1,200 | 160 | 0.9 | 72 |
| 1,200 | 180 | 2.3 | 76 |

Normality of product and reaction rate increased with temperature over the ranges tested. The dodecene utilized was fractionated from a $C_{11}$–$C_{14}$ blend, and was composed of 96–7% $C_{12}$ (olefin and paraffin), and had 1.65% paraffin in the $C_{12}$ fraction and 10.2% 1-isomer in the $C_{12}$-olefin.

EXAMPLE 3

Utilizing the procedure and reaction mixture of Example 2, and a temperature of 180° C., results at different pressures were as follows:

TABLE 2

| Pressure (psi) | K ($hr^{-1}$) | Normal Content of Ester (%) |
|---|---|---|
| 1,200 | 2.3 | 76 |
| 1,500 | 2.2 | 75 |
| 2,000 | 2.7 | 73 |
| 3,000 | 4.3 | 68 |

While increased pressure improved the reaction rate, it also caused a decline in normal content of the ester product.

EXAMPLE 4

Utilizing the procedure and organic components of the reaction mixture as in Example 2, results at 180° C. with different cobalt concentrations at different pressures were as follows:

TABLE 3

| Cobalt (wt.%) | Pressure (psi) | K ($hr^{-1}$) | Normal Content of Ester (%) |
|---|---|---|---|
| 2 | 1,200 | 2.3 | 76 |
| 4 | 1,200 | 4.8 | 74 |
| 2 | 3,000 | 4.3 | 68 |
| 4 | 3,000 | 5.9 | 68 |

EXAMPLE 5

A hydroesterification was carried out with varying cobalt concentrations as set forth in Table 4 below.

TABLE 4

Effect of Cobalt Concentration on Reaction Rate and Cobalt Separation for Recycle
Feed to Reactor: Cobalt charged as $Co_2(CO)_8$, pyridine 36 ml. methanol 36 ml, mixed isomers of linear dodecene 78 ml.
Operating Conditions: 180° C., 1500 psig (ca 5% $H_2$ rest CO)
Separation Procedure following reaction: After cooling reaction, mixed heptane with hydroesterification reactor product at a 1:1 weight basis.

| Cobalt in feed | | Run Time(min) | % Conversion of Olefins | First Order rate const k, $hr^{-1}$ | Separation[1] | | | | |
|---|---|---|---|---|---|---|---|---|---|
| | | | | | Frac. after Hc Addition Upper Phase | Lower Phase | % Co in each phase | | gms Co in Upper Phase |
| Wt% | Gms | | | | | | Upper | Lower | |
| 4 | 5.4 | 30 | 95 | 8 | 79.5 | 20.5 | 1.3 | 98.7 | 0.07 |
| 2-½ | 3.3 | 50 | 95 | 3.6 | 85 | 15 | 3.1 | 96.9 | 0.10 |
| 1 | 1.3 | 120 | 93 | 1.5 | 93.5 | 6.5 | 15. | 85. | 0.19 |

[1]Cobalt analyzed in upper and lower phase by colormetric technique.
[2]Even at this high temperature and modest pressure cobalt was stable at both 2-½ and 4 wt % cobalt (i.e. no evidence of cobalt metal formation).

The rate of hydroesterification is shown to be considerably higher at the higher cobalt concentrations. Also, the cobalt remained stable, even at the higher concentrations, although the pressure was a moderate 1500 psi gauge. From literature stability curves, one could have concluded that the cobalt carbonyl should have been unstable at the higher concentrations. At the 2½ and 4 wt % cobalt concentrations, better than 95% of the cobalt separated into the lower phase, which could be recycled to the reactor. At the 1% level, only 85% of the cobalt was present in the lower phase with 15% still in the upper phase. This would represent a commercially unacceptable level of cobalt in the upper phase, as it is to be subjected to distillation directly after separation in the process. The presence of such amounts of cobalt in the distillation contributes to foaming and high boiler formation. Also, such an amount of cobalt represents a substantial loss of cobalt, or indicates the necessity of an additional recovery and catalyst regeneration procedure.

EXAMPLE 6

A hydroesterification was conducted under the general conditions of Example 1 utilizing dodecene and 4% by weight cobalt catalyst, and utilizing an equal weight of heptane for phasing purposes. The upper ester containing phase was then distilled using a spinning band column with about 1 ml. hold-up and employing a 1/1 reflux ratio. The distillation feed contained 0.028% cobalt, 2.9% methanol, 60.6% heptane, 8.5% pyridine and 25.6% ester. Methanol, along with small amounts of heptane and pyridine was distilled over at atmospheric pressure and a temperature of 95° C.; then 58.8 grams, mostly heptane, was distilled at 24° C. and 4 mm. Hg. A product cut, 32.94 grams, was then obtained at 100° C. and 0.5 mm Hg and was 88.7% ester. A 1.22 gram distillation heel was left, containing 2.5% ester, and 21.5% of corresponding acid. The product isolation was good, with no significant problem from the very small amount of cobalt present during distillation. The amount of distillation heel indicates a selectivity, based on olefin, loss to high boilers of 3.3%. If the ester and acid can be recovered the loss is reduced to 2.5%. It is desirable to keep high boiler loss on the overall hydroesterification and product recovery process to low values, less than 5% based on olefin, and preferably even lower losses.

EXAMPLE 7

The organic phase obtained from a hydroesterification and separation was subjected to distillation. Dodecene had been utilized for phasing in the separation, so was present in large amount. The 102 grams of material was 1.2% unknown low boilers, 2.6% methanol, 7.3% pyridine, 38.7% isomerized dodecenes, 1.8% $C_{13}$-aldehydes, 45.1% $C_{13}$-esters (65% linear), 0.5% $C_{13}$-acetal, about 4% high boilers and 0.23% cobalt. The low boilers and methanol were substantially removed at atmospheric pressure, followed by most of the pyridine at 60° C. and 150 mm Hg and some dodecene, and then additional dodecene at 119° C., 40 mm Hg, followed by aldehyde at 154° C., 43 mm Hg. Three cuts of ester were taken at 174°-185° C., 43-44 mm Hg, with the normality of the ester being respectively 24%, 77% and 98%. The second ester cut, 22 grams, was 98.2% ester, and the other smaller cuts were 94.5-95% ester. A distillation heel, 9.50 grams, was 1.82% cobalt and about 39% ester. The bulk of the cobalt was in the heel, with distillation cuts having only small, less than 5 ppm cobalt, except for the pyridine cut which inexplicably contained 154.3 ppm.

EXAMPLE 8

An isomerized dodecene, mainly internal olefin, was hydroesterified in accordance with Example 1, utilizing 4% cobalt and obtaining 94.6% conversion in 30 minutes. Heptane was added in equivalent amount to the reaction mixture, causing phasing, with 4.7:1 the weight ratio of upper to lower phase. The lower phase, containing 99% of the total cobalt, was recycled with fresh olefin, methanol and pyridine to produce 93% conversion of olefin. Heptane was again added, giving phases with a 5:1 weight ratio, and the lower phase was recycled with fresh components to give 90.6% conversion of olefin. The conditions for the recycle reactions were duplicated to the extent feasible using the analysis of liquid reactor products. The catalyst retains its activity and needs no re-activation before use in the recycle reaction.

EXAMPLE 9

Hydroesterification products from reactions under similar conditions were utilized in separation procedures. The products were obtained from procedures using 4% cobalt, 1500 psi gauge, 180°–200° C., and about 94% conversion, and contained about 10% methanol, 25% pyridine, 45% ester and 4% cobalt. Heptane was added in varying ratios to the products, with results as follows:

| Heptane/Product (by weight) | % Total Cobalt Recovered in Lower Phase |
|---|---|
| 0.12 | 89.5 |
| 0.25 | 92.3 |
| 0.49 | 97.2 |
| 1 | 98 |

Cobalt recovery improves with increasing quantity of heptane, but there is little benefit to be gained by increases above unity.

While the invention has been mainly illustrated with batch reactions, it is contemplated that in commercial production a continuous process would ordinarily be employed. A hydroesterification reactor can be used at 180° C. and 1500 psi gauge with 100 lbs. of olefin feedstock, 50.7 lbs. methanol, 59.5 lbs. pyridine, and 48 lbs. carbon monoxide containing 0.02 lbs. hydrogen. The olefin is almost entirely fresh feedstock, while large portions of the carbon monoxide and methanol are provided by recycle from downstream separation, distillation and hydrolysis procedures. Cobalt present in the reactor in a 9.8 lbs. amount, as catalyst, with 9.7 lbs. provided by recycle, and 0.1 lb. as added material. The discharge from the reactor goes to a de-gassing vessel, from which carbon monoxide is recycled to the reactor. The reaction mixture, 268.8 lbs., then enters catalyst recovery, and 258.2 lbs. of petroleum ether is added to the reaction mixture, causing phasing, and the lower phase, containing 9.7 lbs. cobalt, is recycled to the reactor, along with methanol, pyridine, carbon monoxide, and a small amount of petroleum ether. The upper ester containing phase, 440.9 lbs. and containing only 0.1 lb. cobalt, is then charged to distillation columns, from which low boilers and methanol are removed, followed by petroleum ether and pyridine. The petroleum ether (258.2 lbs.) is recycled to catalyst recovery, and the pyridine to the hydroesterification reactor. The residual crude ester in the distillation bottoms, 118.2 lbs. is then hydrolyzed and the organic phase from the hydrolyzer is charged to a distillation column to remove small amounts of olefin, paraffin and ester, leaving the carboxylic acid product. The aqueous phase from the hydrolyzer is subjected to distillation with the methanol in the overhead being recycled to the hydroesterification, while the bottoms water is recycled to the hydrolyzer. As described above, 9.7 lbs. cobalt is recovered for recycle, leaving 0.1 lb. cobalt in the organic phase, and this approximately 0.1 lb. is carried through the subsequent steps until purged with high boilers from the distillation column following removal of lower boiling components from the carboxylic acid product and distillation of such product. The process will produce 108 lbs. of the carboxylic acid product, while approximately 4.4 lbs. of high boilers are purged after being carried through from the various distillation and other steps. The small 0.1 lb. amount of cobalt is small enough to avoid significant distillation problems and avoid unwanted production of high boilers in the distillations. In the described process, the 100 lbs. olefin will include about 1.5 lbs. unreactive olefin which is carried through the various steps and, after the hydrolysis step, distilled over with olefin, aldehyde, etc.

In the continuous procedure described above, the ester was completely hydrolyzed prior to recovery. If desired, the ester itself can be recovered by distillation and utilized as such, or subjected to subsequent hydrolysis if the acid is desired and various components can be recycled as in the above procedure. As a useful alternate, the ester product can be subjected to partial selective hydrolysis, to obtain a product having high normality acids suitable for soap material, and then the residue of the ester can be hydrolyzed to produce acid of lesser normality suitable for various industrial purposes. Components from these hydrolysis steps can be recycled to the hydroesterification and separation steps as in the above procedure. The use of hydrolysis to achieve a separation of high and low normality acids is described in a copending application Ser. No. 000,451, of A. John Solodar, filed Jan. 2, 1979 and the procedures so described can be employed for hydrolysis in processes utilizing the present invention.

What is claimed is:

1. A process of hydroesterifying internal olefins to produce carboxylic acid esters of high normality by reaction of olefin, carbon monoxide and alcohol which comprises reacting same in the presence of a cobalt catalyst and a pyridine promoter at temperatures of about 170° to about 200° C. and pressures of about 1200 psi gauge to 1800 psi gauge, with cobalt constituting 2% to 6% by weight of the reaction mixture and the combination of cobalt concentration, temperature and pressure being such that the reaction rate is at least $k=4$ $hr^{-1}$ and the ester product normality over 70%, adding a large amount of hydrocarbon to the resulting reaction product mixture thereby causing phasing, separating the phases with one phase containing substantially all the ester product, and the other phase containing in excess of 90% of the cobalt catalyst, and recycling the catalyst to the reaction.

2. The process of claim 1 in which the ester containing layer contains only a very small amount of cobalt catalyst, and components less volatile than the ester are separated therefrom by distillation.

3. The process of claim 1 in which a mixture of $C_{11}$ to $C_{13}$ olefins is reacted.

4. The process of claim 1 in which pyridine is present in molar ratio to cobalt of about 2 to about 10, and alcohol is present in molar ratio to olefin of about 2 to about 5.

5. The process of claim 1 in which hydrogen is present in molar ratio to carbon monoxide in the range of about 0.02 to 0.1.

6. The process of claim 1 in which the alcohol is a lower alkanol.

7. The process of claim 1 in which the alcohol is methyl alcohol.

8. The process of claim 1 in which internal olefins are reacted in the presence of pyridine in molar ratio to cobalt of about 2 to about 10, methanol in molar ratio to olefin of about 2 to about 5, and hydrogen in molar ratio to carbon monoxide of 0.02 to 0.1.

9. The process of claim 8 in which at least about 1 part hydrocarbon is added per part reaction product mixture and the resulting phase containing ester product contains less than 500 ppm cobalt, and distillation is employed for product separation with less than 5% loss to high boilers, based on olefin.

10. The process of claim 1 in which alkane hydrocarbon is used.

11. The process of claim 1 in which more than 95% of the cobalt catalyst is separated in the phase other than that containing the ester product and the ester product phase contains no more than 0.1% by weight cobalt and components are distilled therefrom with little by-product formation.

* * * * *